United States Patent [19]
Fujisaki et al.

[11] Patent Number: 5,599,505
[45] Date of Patent: Feb. 4, 1997

[54] CHEMICAL ANALYSIS ELEMENT CARTRIDGE WITH CAPPING MEMBER

[75] Inventors: Yasushi Fujisaki, Saitama-ken; Yoshihiro Seto; Seiichi Watanabe, both of Kanagawa-ken; Kaoru Terashima, Saitama-ken, all of Japan

[73] Assignee: Fuji Photo Film Co., Ltd., Kanagawa, Japan

[21] Appl. No.: 527,626

[22] Filed: Sep. 13, 1995

[30] Foreign Application Priority Data

Sep. 16, 1994 [JP] Japan ................... 6-221763

[51] Int. Cl.$^6$ ................................................. B01L 9/00
[52] U.S. Cl. ..................... 422/104; 422/58; 422/102; 436/46; 206/499; 220/324; 220/729; 220/784
[58] Field of Search .................. 422/63, 64, 66, 422/99, 102, 103, 104, 58; 436/46, 43, 48; 435/905; 206/556, 499, 718; 220/305, 306, 324, 676, 729

[56] References Cited

U.S. PATENT DOCUMENTS

| | | | |
|---|---|---|---|
| 4,187,077 | 2/1980 | Covington et al. | 422/63 |
| 4,346,817 | 8/1982 | Karcher | 221/718 |
| 4,353,481 | 10/1982 | Tando | 221/251 |
| 4,512,952 | 4/1985 | Blanding et al. | 422/63 |
| 4,589,547 | 5/1986 | Stewart et al. | 206/328 |
| 5,053,198 | 10/1991 | Quenin | 422/64 |
| 5,075,079 | 12/1991 | Kerr et al. | 422/64 |
| 5,154,889 | 10/1992 | Muraishi | 422/65 |
| 5,207,345 | 5/1993 | Stewart et al. | 220/254 |
| 5,232,091 | 8/1993 | Hennessy et al. | 206/331 |
| 5,384,096 | 1/1995 | Burns | 422/102 |

FOREIGN PATENT DOCUMENTS 0555654  8/1993  European Pat. Off. .

Primary Examiner—Long V. Le
Attorney, Agent, or Firm—McAulay Fisher Nissen Goldberg & Kiel, LLP

[57] ABSTRACT

A chemical analysis film cartridge has a box-like cartridge body in which a plurality of chemical analysis films are stacked. The chemical analysis films are taken out one by one through a take-out port formed in one end of the cartridge body. The take-out port has a first opening portion which is opened through a first side wall of the cartridge body and through which one chemical analysis film can be passed and a second opening portion which opened through one end face of the cartridge body. A first engagement portion is formed on the outer surface of the first side wall near the first opening portion and a second engagement portion is formed on the outer surface of a second side wall opposed to the first side wall. A capping member having third and fourth engagement portions is removably mounted on the cartridge body to cover the first and second opening portions of the take-out port with the third and fourth engagement portions respectively engaged with the first and second engagement portions. The capping member is provided with a protruding portion which projects into the cartridge body and pushes inside the chemical analysis films away from the first opening portion.

6 Claims, 8 Drawing Sheets

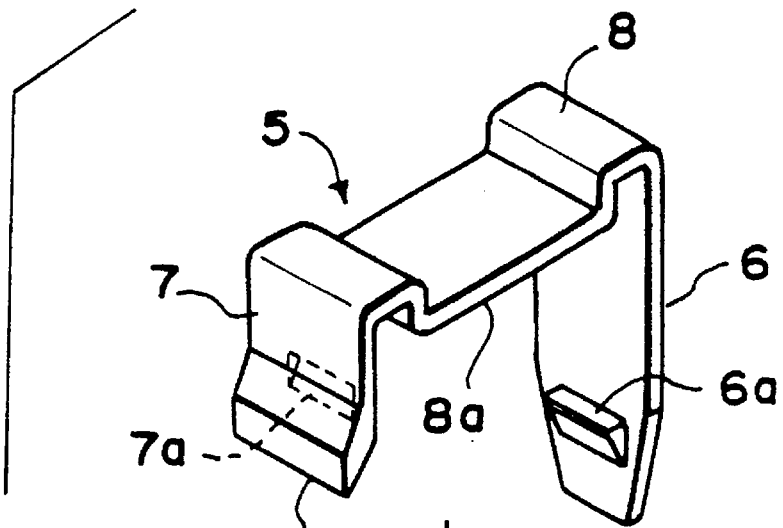
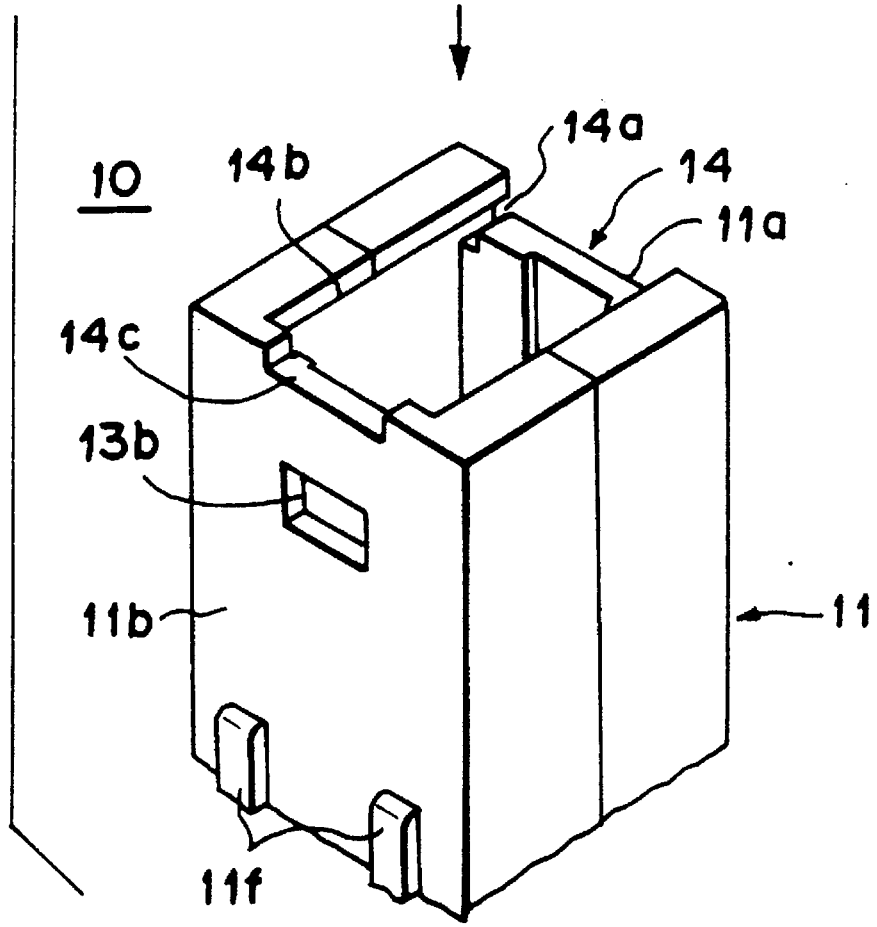
FIG.4

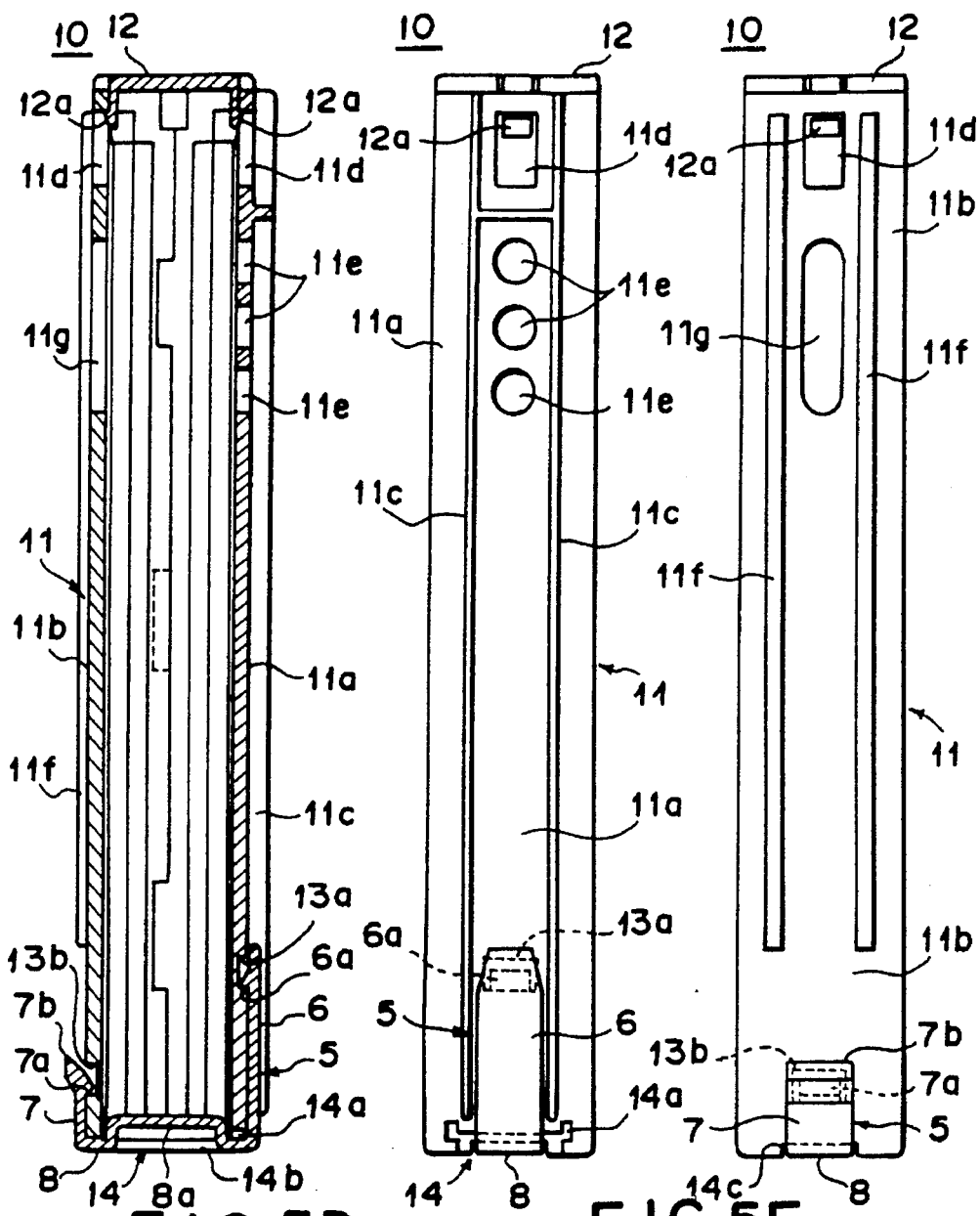
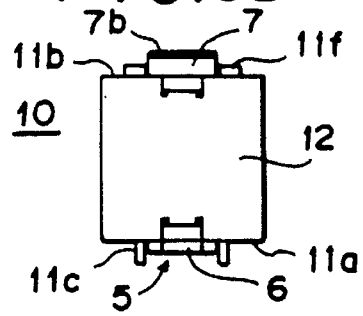
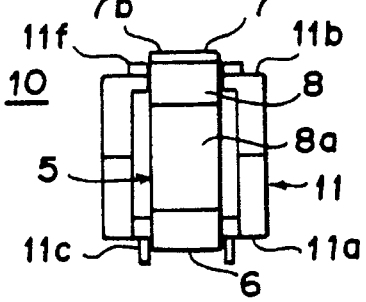

CHEMICAL ANALYSIS ELEMENT CARTRIDGE WITH CAPPING MEMBER

BACKGROUND OF THE INVENTION

1. Field of the Invention

This invention relates to a chemical analysis element cartridge in which a plurality of chemical analysis elements each having thereon a reagent layer whose optical density changes by chemical reaction, biochemical reaction, immunoreaction or the like with a specific biochemical or chemical component contained in a sample liquid such as blood or urine are stored and taken out one by one, and more particularly to such a chemical analysis element cartridge provided with a capping member for preventing the chemical analysis elements from slipping out of the cartridge.

2. Description of the Related Art

There have been put into practice various "dry-to-the-touch" chemical analysis elements with which the content of a specific chemical component contained in a sample liquid, the activity thereof, or the content of a solid component can be quantitatively analyzed by only spotting a droplet of the sample liquid on the element. For example, there has been known an integrated multi-layered chemical analysis film. Further a chemical analysis film formed of filter paper and having one or more layers has been proposed and partly put into practice.

When quantitatively analyzing the chemical components or the like contained in a sample liquid using such a chemical analysis film, a droplet of the sample liquid is spotted on the film (on the spreading layer when the film is provided with a spreading layer and directly on the reagent layer when the film is not provided with a spreading layer) and is held at a constant temperature for a predetermined time (incubation) in an incubator so that coloring reaction (coloring matter generating reaction or color change reaction of the coloring substance in the reagent layer) occurs, and the optical density of the color formed by the coloring reaction is optically measured. That is, measuring light containing a wavelength which is preselected according to the combination of the component to be analyzed (sometimes will be referred to as "analyte", hereinbelow) and the reagent contained in the reagent layer of the film is projected onto the film and the optical density of the film is measured. Then the concentration or the activity of the analyte is determined on the basis of the optical density using a calibration curve or a standard curve which represents the relation between the concentration (content) of the analyte and the optical density.

The integrated multi-layered chemical analysis film generally comprises a support sheet of organic polymer and at least one reagent layer formed on the support sheet. Preferably a spreading layer is formed over the reagent layer. The chemical analysis film is generally in the form of a film chip of a predetermined shape such as square or rectangle. The film chip is sometimes provided with a frame of organic polymer or the like for facilitating automated handling of the film chip and sometimes used as it is without frame. The chemical analysis film with a frame is generally referred to as "a chemical analysis slide" and that without frame is generally referred to as "a frameless chemical analysis film".

In this specification, the term "chemical analysis element" should be broadly interpreted to include the frameless chemical analysis film, the chemical analysis slide and the single-layered or multi-layered chemical analysis film formed of filter paper (with or without frame) as well as an electrolyte analysis slide for quantitatively analyzing the activity of particular ionic substances contained in a sample liquid and other like elements and devices for various analyses.

For instance, in Japanese Utility Model Publication 57(1982)-53271 (U.S. Pat. No. 4,151,931), there is disclosed a chemical analysis element cartridge in which a plurality of the chemical analysis elements are stacked and from which the chemical analysis elements are taken out one by one. In the cartridge, a plurality of chemical analysis elements are stacked in a cartridge body which is provided with an element take-out port in a side surface of the upper portion thereof and the uppermost element is pushed out and fed to a chemical analysis apparatus through the element take-out port by a pusher blade which is moved in a horizontal direction. The stack of the elements are supported on a pressing member which is disposed in the cartridge body and is permitted to move only upward by a ratchet mechanism. The pressing member is lifted upward by a plunger inserted into the cartridge body from below so that the stack of the elements is moved upward by a distance equal to the thickness of one element and the second uppermost element is brought to the element take-out port each time the uppermost element is pushed out.

Further there has been known a technique of pressing a stack of chemical analysis elements toward a element take-out port by a pressing member which is urged an elastic body or a spring and taking out the chemical analysis elements one by one through the element take-out port as disclosed, for instance, in Japanese Unexamined Patent Publication Nos. 5(1993)-188058 and 1(1989)-87438 (corresponding to European Patent Laid Open No. 304 838A), European Patent Laid Open No. 567 067A and the like.

However the structures of the cartridge described above is disadvantageous in that when an impact acts on the cartridge during transfer or the like, the chemical analysis elements in the cartridge can move in the cartridge and there is a possibility of the element slipping out of the cartridge through the element take-out port. Further even if the element does not slip out of the cartridge, shift of the position of the elements in the cartridge can adversely affect taking out the elements from the cartridge, transfer of the element and the like, which can result in inaccurate measurement.

That is, when a chemical analysis element projects outside the cartridge, the element can impact against a cartridge holding portion of a biochemical analysis apparatus, which can result in damage on the element or positioning the element in a wrong position. Even if the cartridge can be positioned in place, there is a fear of jam during taking out and transferring the element from the cartridge if the elements are not in the regular place in the cartridge.

Further when the elements are not in the regular place in the cartridge, there is a fear that the sample liquid cannot be spotted in the regular position on the element, which results in ununiform spread of the sample liquid on the element and in deterioration in accuracy of measurement.

SUMMARY OF THE INVENTION

In view of the foregoing observations and description, the primary object of the present invention is to provide a chemical analysis element cartridge provided with a capping member which holds the chemical analysis elements in the regular position to prevent them from slipping out of the cartridge when an impact acts on the cartridge during transfer or the like.

The chemical analysis element cartridge in accordance with the present invention has a box-like cartridge body in which a plurality of chemical analysis elements are stacked. The chemical analysis elements are taken out one by one through a take-out port formed in one end of the cartridge body. The take-out port has a first opening portion which is opened through a first side wall of the cartridge body and through which one chemical analysis element can be passed and a second opening portion which opened through one end face of the cartridge body. A first engagement portion is formed on the outer surface of the first side wall near the first opening portion and a second engagement portion is formed on the outer surface of a second side wall opposed to the first side wall. A capping member having third and fourth engagement portions is removably mounted on the cartridge body to cover the first and second opening portions of the take-out port with the third and fourth engagement portions respectively engaged with the first and second engagement portions. The capping member is provided with a protruding portion which projects into the cartridge body and pushes inside the chemical analysis elements away from the first opening portion.

Preferably the capping member is substantially U-shaped and has first and second portions connected to opposite ends of the protruding portion. The first portion lies on the first side wall near the first opening portion and the second portion lies on the second side wall when the capping member is on the cartridge body with the third and fourth engagement portions respectively engaged with the first and second engagement portions. Preferably the first and second engagement portions are in the form of recesses respectively formed on the outer surfaces of the first and second side walls, and the third and fourth engagement portions are in the form of projections respectively formed on the inner surfaces of the first and second portions of the capping member near or on the ends of the first and second portions.

When the cartridge is transferred with the chemical analysis elements loaded therein, the capping member is mounted on the cartridge body and held thereon by engagement of the first and second engagement portions on the cartridge body and the third and fourth engagement portions on the capping member and the first opening portion is closed by the first portion of the capping member with the stack of the chemical analysis elements pushed away from the first opening portion by the protruding portion of the capping member. Accordingly the chemical analysis elements are held in the regular position and are prevented from slipping out of the cartridge when an impact acts on the cartridge during transfer or the like.

Just before the cartridge is loaded in a biochemical analysis apparatus, the capping member is removed, the first and second opening portions are opened and the stack of the chemical analysis elements is moved toward the take-out port so that the first element is positioned in the regular take-out position without entering the first opening portion. Accordingly the cartridge can be smoothly loaded in the cartridge without interference with the cartridge body. Further since the chemical analysis elements are held in the regular position, even the first element can be transferred in the regular manner and the measurement can be effected accurately, whereby a high reliability can be obtained.

Preferably the first portion of the capping member is longer than the second portion and the free end portion of the second portion extends obliquely outward so that the end of the second portion is positioned away from the second side wall.

The longer first portion enhances the force holding the capping member on the cartridge body and the shorter second portion facilitates removal of the capping member from the cartridge body, whereby capping member holding force and easiness in removing the capping member are both improved.

When the capping member is removed from the cartridge body, the second portion is first expanded outward to disengage the fourth engagement portion from the second engagement portion and then moved toward the take-out port to disengage the first engagement portion from the third engagement portion. Accordingly when the second portion has an inclined engagement surface facing toward the protruding portion, the fourth engagement portion can be easily disengaged from the second engagement portion by simply moving the second portion toward the take-out port.

Further when the first portion is inserted between a pair of ribs formed on the first side wall to extend in the longitudinal direction of the cartridge body, the first portion is guided by the ribs and mount of the capping member is facilitated and at the same time, the capping member is prevented from moving in a lateral direction and disengaging from the cartridge body.

BRIEF DESCRIPTION OF THE DRAWINGS

FIG. 4 is a perspective view for illustrating the manner of mounting the cap on the cartridge body, FIGS. 5A to 5E are a cross-sectional view, a front view, a rear view, a plan view and a bottom view of the cartridge with the cap.

DESCRIPTION OF THE PREFERRED EMBODIMENT

Figure 1:
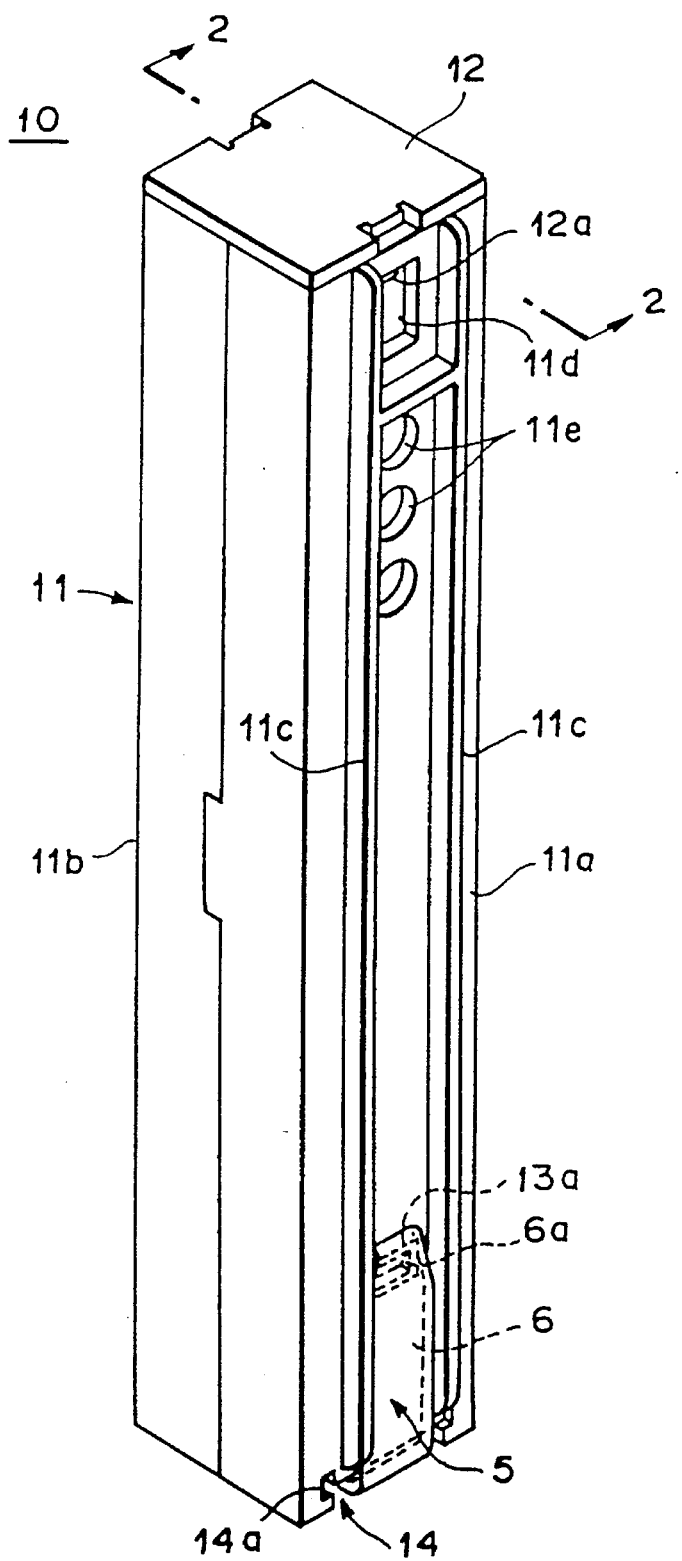
FIG. 1 is a perspective view of a chemical analysis film cartridge in accordance with an embodiment of the present invention.

In FIG. 1, a cartridge 10 in accordance with an embodiment of the present invention comprises a box-like cartridge body 11 in which a plurality of frameless chemical analysis films 1 are stored in a stack. The cartridge body 11 is a rectangular tubular column in shape and is formed by mating together left and right halves. The cartridge body 11 is open at the top thereof and the open upper end is closed with a lid member 12. The stack of the chemical analysis films 1 is inserted into the cartridge body 11 through the upper end.

A chemical analysis film take-out port 14 for taking out the chemical analysis films 1 one by one is formed in the cartridge body 11 at the lower end thereof. The take-out port 14 comprises a first opening portion 14a which is formed in a first side wall 11a of the cartridge body 11 and through which only one chemical analysis film 1 can be passed and a second opening portion 14b which is formed in the bottom of the cartridge body 11 and through which a film take-out suction pad 15 (FIG. 3) is inserted into the cartridge body 11 to attract the lowermost film 1 and hold it under a suction force as will be described in more detail later. As clearly shown in FIG. 4, the second opening portion 14b is connected to the first opening portion 14a at he lower end of the side wall 11a of the cartridge body 11, and a cutaway portion 14c is formed in a second side wall 11b opposed to the side wall 11a. The cutaway portion 14c has a width substantially equal to that of a cap 5 for preventing the film 1 from slipping out of the cartridge body 11.

The thickness of the films 1 varies depending on the analyte to be analyzed with the films 1 and accordingly the dimensions of the first opening portion 14a is set to conform to the thickness of films 1 to be loaded in the cartridge 10.

A film pressing mechanism 16 (FIGS. 2, 3 and 7) for urging the stack of the films 1 toward the take-out port 14 is provided in the cartridge body 11. The film pressing mechanism 16 comprises a film pressing means 17 having a film pressing member 17a which is slidably received in the cartridge body 11 from the top of the cartridge body 11 and presses the stack of the films 1 toward the take-out port 14, a spring 18 which urges the film pressing member 17a toward the take-out port 14, and a stopper 19 which supports the upper end of the spring 18 and is in engagement with the cartridge body 11 to limit a movement of the film pressing member 17a in the direction away from the take-out port 14 as will be described in more detail later.

A pair of ribs 11c are formed on the first side wall 11a of the cartridge body 11 to extend in the longitudinal direction of the cartridge body 11. An opening 11d which is adapted to be engaged with a leg portion 12a of the lid member 12 and three distinguishing holes 11e are formed in the upper portion of the first side wall 11a between the ribs 11c. Each of the three distinguishing holes 11e is a blind hole with a thin bottom in the initial state and the bottom of one of the distinguishing holes 11e is pierced depending on the thickness of the films 1 to be loaded in the cartridge 10, for instance, when the cartridge 10 is assembled. Further a first engagement recess 13a is formed in the lower portion of the first side wall 11a between the ribs 11c near the first opening portion 14a. As clearly shown in FIG. 2, the first engagement recess 13a does not pierce through the side wall but has a thin bottom wall. As shown in FIG. 3, a series of ratchet teeth 11h is formed on each side of the inner surface of the side wall 11a to extend in the longitudinal direction of the cartridge body 11.

As shown in FIG. 5C, a pair of ribs 11f are formed on the second side wall 11b of the cartridge body 11 to extend in the longitudinal direction of the cartridge body 11. The ribs 11f are smaller than the ribs 11c on the first side wall 11a in height and length but larger than the same in width, and a space for facilitating removal of the cap 5 is formed below the lower ends of the ribs 11f. An opening 11d which is adapted to be engaged with a leg portion 12a of the lid member 12 and an elongated through hole 11g are formed in the upper portion of the second side wall 11b between the ribs 11f. The through hole 11g is opposed to the three distinguishing holes 11e in the first side wall 11a. Further a second engagement recess 13b is formed in the lower portion of the second side wall 11b between the ribs 11f near the cutaway portion 14c. As clearly shown in FIG. 2, the second engagement recess 13b does not pierce through the side wall but has a thin bottom wall. As shown in FIG. 3, a series of ratchet teeth 11h is formed on each side of the inner surface of the side wall 11b to extend in the longitudinal direction of the cartridge body 11.

The left and right halves of the cartridge body 11 are formed separately and are fused together into the cartridge body 11. The left and right halves are not separable after once fused together though a parting line is shown in the drawings.

The cap 5 for preventing the film 1 from slipping out the cartridge 10 is removably mounted the cartridge body 11 to close the take-out port 14. The cap 5 is formed of synthetic resin (organic polymer) and has elasticity or resiliency. As shown in FIGS. 4 and 6A to 6H, the cap 5 is generally U-shaped and comprises a first portion 6 fitted on the first side wall 11a, a second portion 7 fitted on the second side wall 11b and a bottom portion 8 fitted on the bottom of the cartridge body 11.

The first portion 6 is provided on the inner side of the end portion thereof with a first engagement projection 6a which is to be brought into engagement with the first engagement recess 13a and the second portion 7 is provided on the inner side of the end portion thereof with a second engagement projection 7a which is to be brought into engagement with the second engagement recess 13b. The first portion 6 is longer than the second portion 7. The bottom portion 8 has a protruding portion 8a which protrudes inward and forms recesses between opposite ends of the bottom portion 8 and the first and second portions 6 and 7 so that the protruding portion 8a projects inward of the cartridge body 11 through the second opening portion 14b with the recesses engaged with the lower ends of the respective side walls 11a and 11b of the cartridge body 11 when the cap 5 is mounted on the cartridge body 11.

The second portion 7 has an extension 7b which extends obliquely outward from the end of the second portion 7 so that the end of the extension 7b is positioned away from the second side wall 11b, when the cap 5 is mounted on the cartridge body 11, to facilitate removal of the cap 5. The surface of the second engagement projection 7a on the second portion 7 inclines toward the end of the second portion 7 and toward the root of the same from the top of the projection 7a. The first portion 6 longer than the second portion 7 is tapered toward its end and the first engagement projection 6a on the first portion 6 has an inclined surface toward the end of the first portion 6. The surface behind the top of the first engagement projection 6a is substantially perpendicular to the inner surface of the first portion 6.

A data recording portion (not shown) such as a bar code representing the production lot, the period of service or properties of the films 1 loaded in the cartridge 10, the analyte to be analyzed by the films 1 or the like is provided on one of the side walls adjacent to the first and second side walls 11a and 11b.

Figure 2:
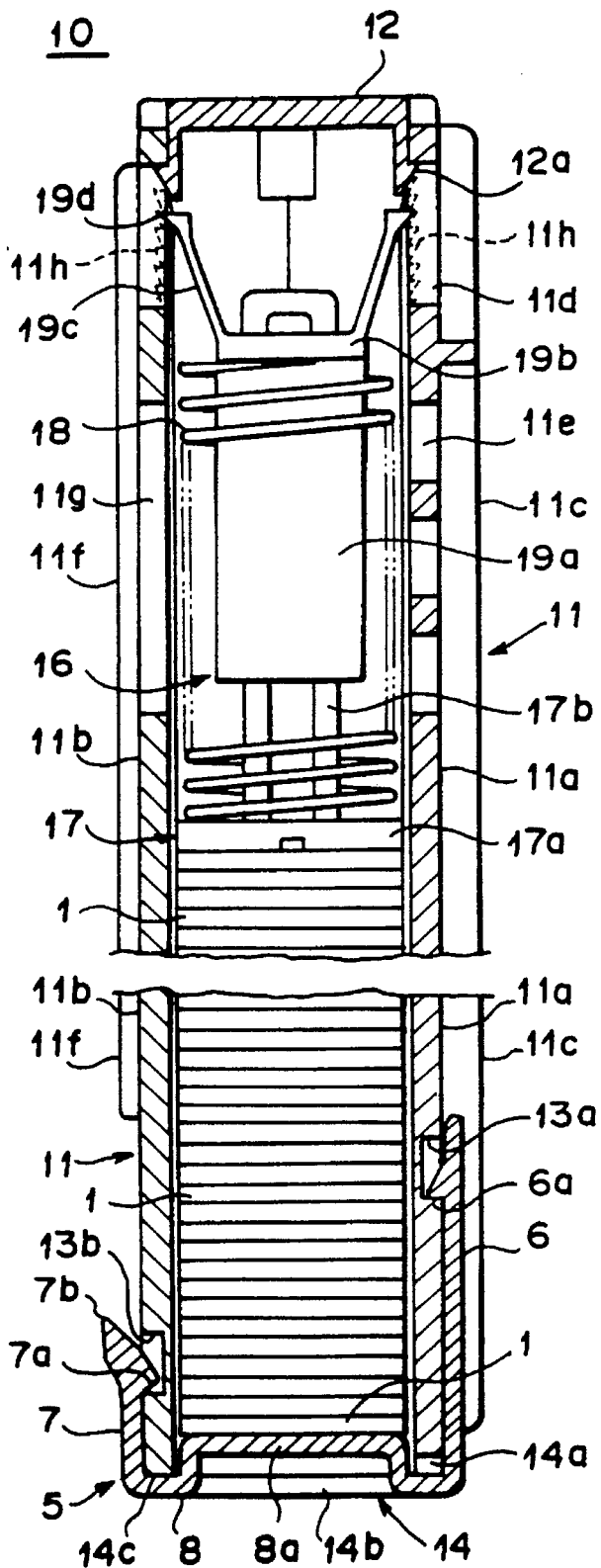
FIG. 2 is a cross-sectional view taken along line 2—2 in FIG. 1.
Figure 3:
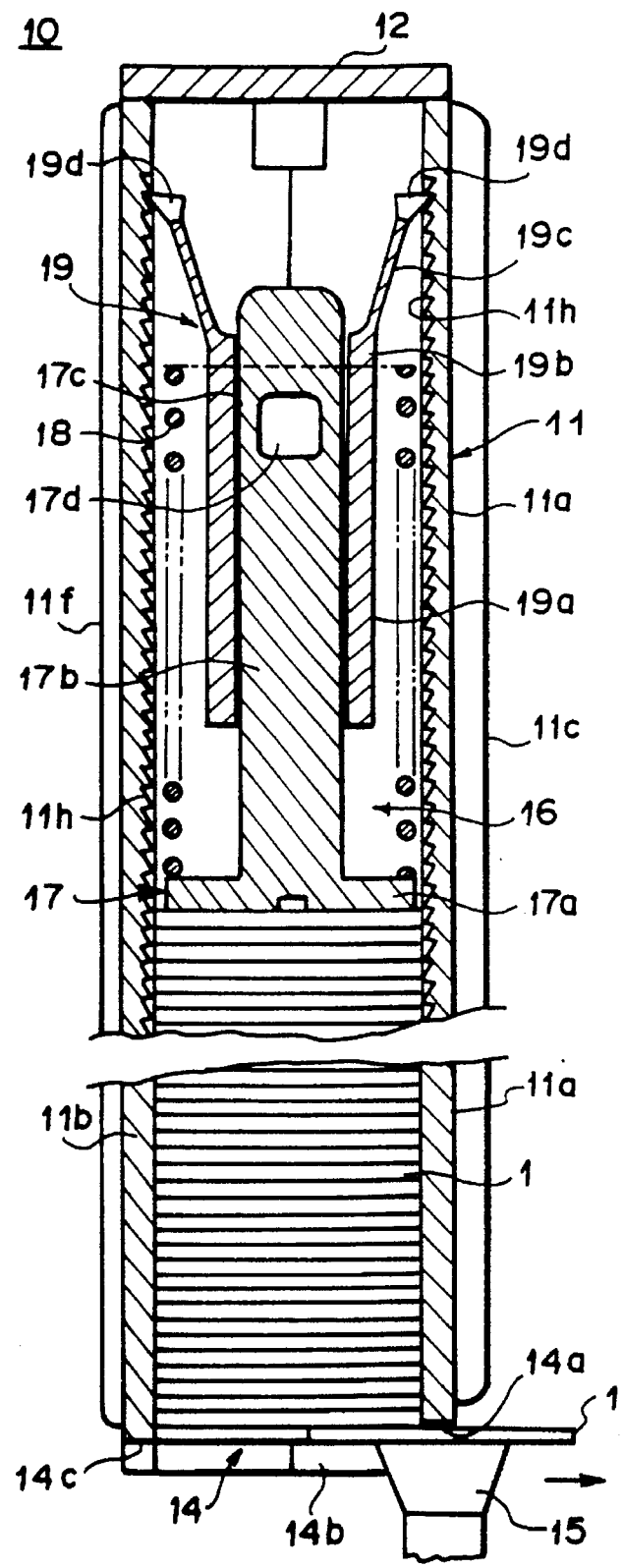
FIG. 3 is a cross-sectional view illustrating the manner of taking out the chemical analysis film from the cartridge.
Figure 6A:
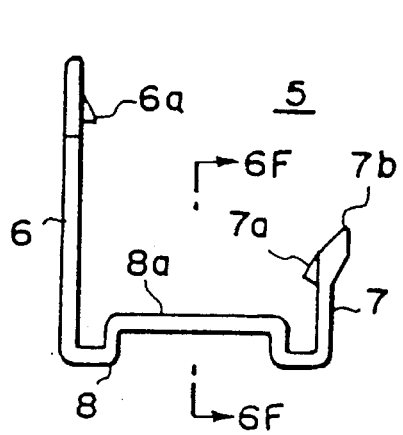
FIG. 6A is a front view of the cap.
Figure 6B:
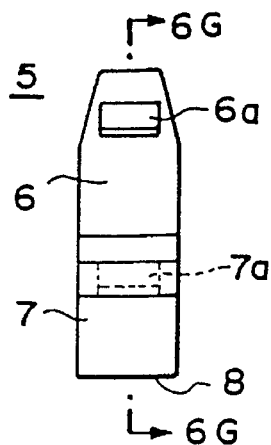
FIG. 6B is a right side view of the cap.
Figure 6C:
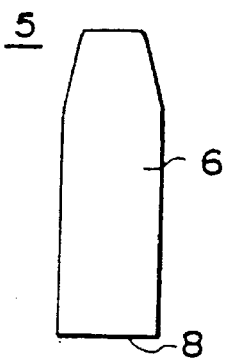
FIG. 6C is a left side view of the cap.
Figure 6D:
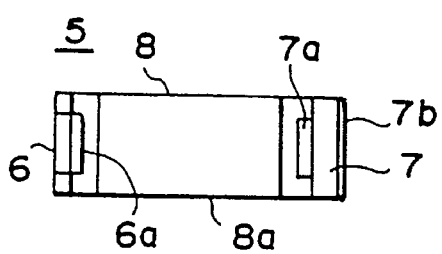
FIG. 6D is a plan view of the cap.
Figure 6G:
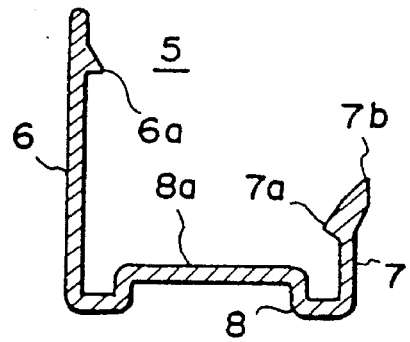
FIG. 6G is a cross-sectional view taken along line 6G—6G in FIG. 6B
Figure 6E:
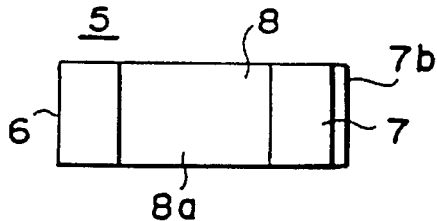
FIG. 6E is a bottom view of the cap.
Figure 6F:
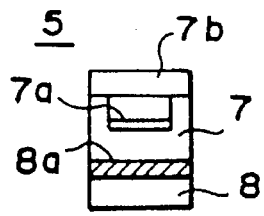
FIG. 6F is a cross-sectional view taken along line 6F—6F in FIG. 6A.
Figure 6H:
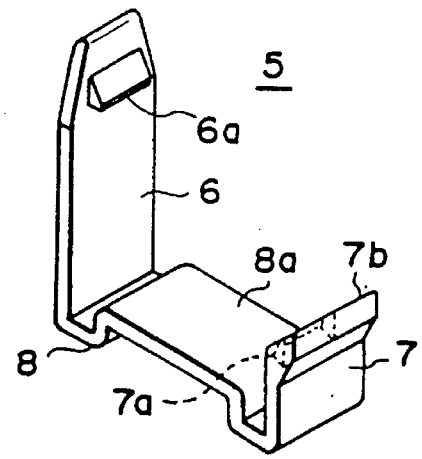
FIG. 6H is a perspective view of the cap.
Figure 7:
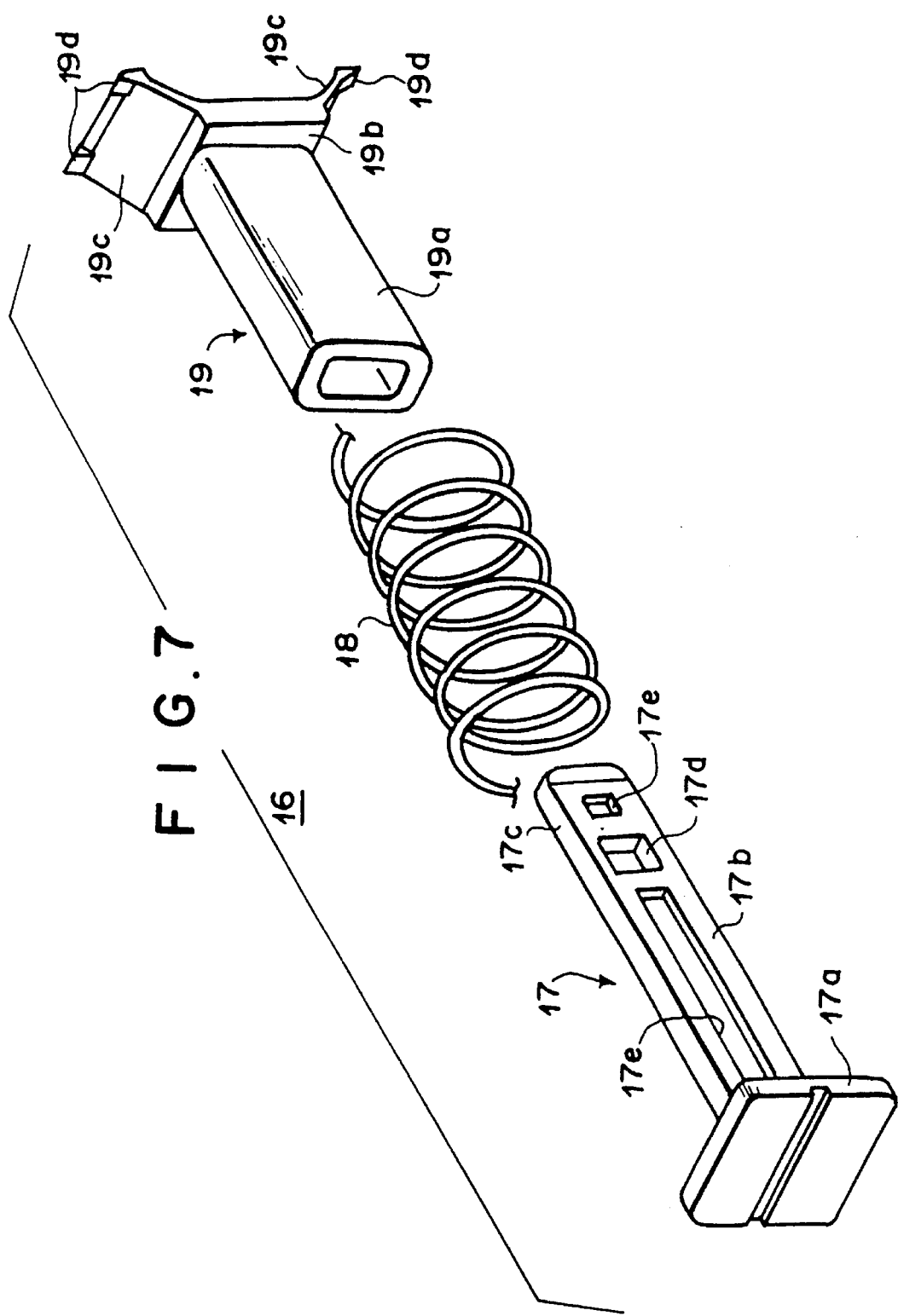
FIG. 7 is an exploded perspective view of the film pressing mechanism.

Referring to FIGS. 2, 3 and 7, the film pressing member 17a of the film pressing means 17 of the film pressing mechanism 16 is a flat plate member and a shank portion 17b which is like a rectangular column projects vertically from the rear face of the plate member. The shank portion 17b is a chamfered rectangle or square in cross-section and the rear end portion 17c of the shank portion 17b forms a handle portion which projects rearward (upward as seen in FIG. 3) from the stopper 19 when the film pressing mechanism 16 is assembled as will be come apparent later. A through hole 17d is formed in the rear end portion 17c and an elongated groove 17e is formed in the side surface of the shank portion 17b.

The stopper 19 comprises a sleeve 19a which is like a rectangular column, a spring retainer 19b which extends laterally from the rear end of the sleeve 19a and supports an end of the spring 18 and a pair of engagement portions 19c which extend obliquely rearward from the spring retainer 19b. The sleeve 19a slidably receives therein the shank portion 17b of the film pressing means 17 and is shorter than the length between the rear end portion 17c of the shank portion 17b and the film pressing member 17a.

Each of the engagement portions 19c is provided on its rear end with a pair of claw portions 19d which are brought into engagement with the ratchet teeth 11h on the inner surface of the cartridge body 11.

The spring 18 is fitted on the shank portion 17b and the sleeve 19a and is compressed between the film pressing member 17a and the spring retainer 19b. In the state before assembly of the film pressing mechanism 16 into the cartridge body 11, the stopper 19 and the pressing member 17a are pressed toward each other compressing the spring 18 until the rear end portion 17c of the shank portion 17b projects rearward from the sleeve 19a and held there by a jig (not shown) passed through the through hole 17d in the rear end portion 17c. Thus the film pressing mechanism 16 is held in a state of an assembled unit.

Figure 8A:
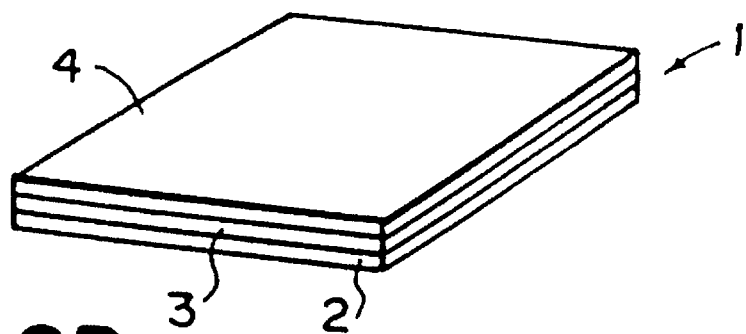
FIGS. 8A to 8C are perspective views showing the frameless chemical analysis films in different states.
Figure 8B:
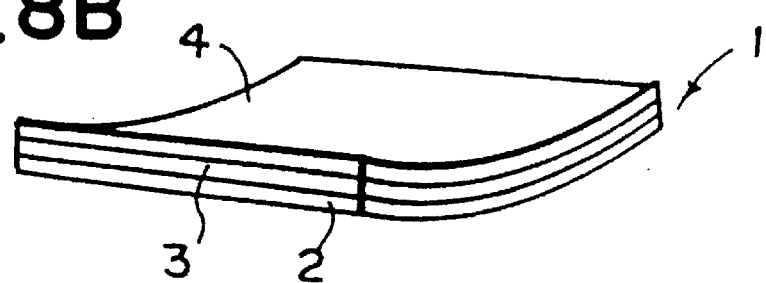
Figure 8C:
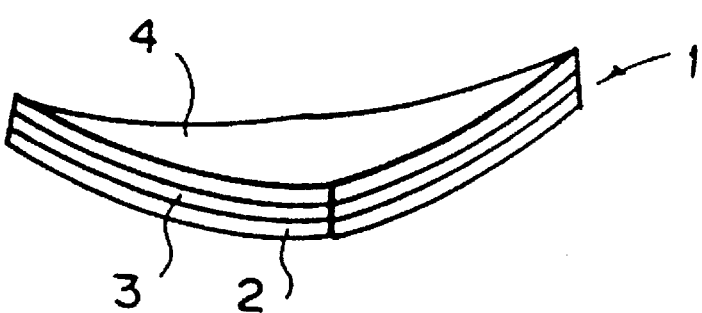

As shown in FIGS. 8A to 8C, the frameless chemical analysis film 1 loaded in the cartridge 10 comprises, for example, a light-transmissive support sheet 2 formed of plastic sheet such as of polyethylene terephthalate, polystyrene or the like, a reagent layer 3 and a spreading layer 4. That is, the film 1 is formed by coating or bonding the reagent layer 3 on the support sheet 2 and laminating the spreading layer 4 on the reagent layer. As described above, the frameless chemical analysis film 1 is not provided with any frame.

The spreading layer 4 is formed of a material resistant to rubbing such as woven or knitted fabric (or cloth) of synthetic fiber such as polyethylene terephthalate or of blend of natural fiber and synthetic fiber, or paper, and functions as a protective layer. Further the spreading layer 4 causes sample liquid applied thereto to uniformly spread over the reagent layer 3.

Under the normal humidity conditions, the frameless chemical analysis film 1 is substantially flat as shown in FIG. 8A. The film 1 is stored in a dry environment (e.g., in an environment where the humidity is not higher than 20%) in order to suppress chemical reaction or immunoreaction, and in such a dry state, the film 1 is warped toward the spreading layer 4 as shown in FIG. 8B or 8C. In the state shown in FIG. 8B, the film 1 is curled in one direction and in the state shown in FIG. 8C, the film 1 is curled in a plurality of directions.

The cap 5 is mounted before or after loading the frameless chemical analysis films 1 and setting the film pressing mechanism 16 in the cartridge body 11.

A plurality, e.g., 100 or 50, of chemical analysis films 1 are stacked and the stack of the films 1 are inserted into the cartridge body 11 through the open top end of the cartridge body 11 with the lid member 12 removed. At this time, a small space is formed between adjacent films 1 due to warp or curl of the films 1 described above. This gives elasticity or resiliency to the stack of the films 1 against compression.

The film pressing mechanism 16 held by the jig in the assembled state is inserted into the cartridge body 11 with the handle portion (rear end portion 17c projecting rearward from the sleeve 19a) caught by an assembling means (robot hand) to a position where the film pressing member 17a is brought into contact with the uppermost film or short of the uppermost film while bringing the claw portions 19d on the engagement portions 19c into engagement with the ratchet teeth 11h on the inner surface of the cartridge body 11. Then the handle portion is released and the lid member 12 is mounted on the cartridge body 11. When the handle portion is released, the film pressing member 17a is moved toward the stack of the films 1 and presses the stack toward the take-out port 14 under the force of the spring 18. The initial position of the stopper 19 relative to the cartridge body 11 is adjusted according to the height of the stack of the films 1 which varies with the thickness of each film and/or the number of the films 1 in the stack.

The cap 5 is mounted on the bottom of the cartridge body 11 to cover the take-out port 14 as shown in FIG. 4. At this time, the first and second portions 6 and 7 of the cap 5 are easily deformed to diverge away from each other by virtue of the inclined surfaces on the engagement projections 6a and 7a when the first and second portions 6 and 7 are brought into contact with the lower edge portions of the first and second side walls 11a and 11b, and then slid along the side walls 11a and 11b while the first portion 6 is guided by the ribs 11c until the engagement projections 6a and 7a are engaged with the engagement recesses 13a and 13b, respectively. The perpendicular rear surface of the first engagement projection 6a enhances the engaging force between the first engagement projection 6a and the engagement recesses 13a.

In this state, the protruding portion 8a of the bottom portion 8 of the cap 5 projects inward of the cartridge body 11 through the second opening portion 14b and pushes the lowermost film 1 away from the first opening portion 14a, whereby all the films 1 in the stack are opposed to the wall of the cartridge body 11. The cartridge 10 is transferred in this state. Accordingly even if an impact acts on the cartridge 10, for instance, when the cartridge 10 is dropped, none of the films 1 can move into the first opening portion 14a and slip out of the cartridge body 11.

Just before the cartridge 10 is loaded in a biochemical analysis apparatus, the cap 5 is removed from the cartridge body 11. When removing the cap 5 from the cartridge body 11, the end of the extension 7b of the second portion 7 is pushed downward with a finger. Since the end portion of the extension 7b is away from the side wall 11b, a finger can be easily applied to the end portion and since the surface of the second engagement projection 7a on the second portion 7 inclines toward the root of the second portion 7, the second portion 7 can be easily deformed outward so that the second engagement projection 7a is disengaged from the second engagement recess 13b. After the second engagement projection 7a is disengaged from the second engagement recess 13b, the second portion 7 is moved toward the bottom of the cartridge body 11 while deforming the cap 5, and the protruding portion 8a of the bottom portion 8 is moved away from the second opening portion 14b, and finally the first engagement projection 6a on the first portion 6 is disengaged from the first engagement recess 13a. Thus the cap 5 is easily removed from the cartridge body 11.

When the cap 5 is removed, the first opening portion 14a and the second opening portion 14b of the take-out port 14 are opened and the lowermost film 1 which has been held away from the first opening portion 14a by the protruding portion 8a is moved to a position where it is in alignment with the first opening portion 14a. In this state, the cartridge 10 is loaded in the biochemical analysis apparatus and the films 1 are taken out one by one by said suction pad 15.

The longer first portion 6 of the cap 5 enhances the force holding the cap 5 on the cartridge body 11 and the shorter second portion 7 facilitates removal of the cap 5 from the cartridge body 11, whereby cap holding force and easiness in removing the cap are both improved.

Though in the embodiment described above, the structure for holding the cap 5 on the cartridge body 11 comprises recesses (the engagement recesses 13a and 13b) formed on the cartridge body 11 and projections (the engagement projections 6a and 7a) formed on the cap 5, the structure may be variously changed. For example, engagement projections may be formed on the cartridge body 11 and engagement recesses or openings may be formed on the cap 5.

Though, in the embodiment described above, the frameless chemical analysis films are loaded in the cartridge 10, other chemical analysis elements such as the chemical analysis slide and the single-layered or multi-layered chemical analysis film formed of filter paper (with or without frame) as well as an electrolyte analysis slide may be loaded in the cartridge 10 of the present invention. Further the elements may be taken out by various means other than the suction pad 15 described above. For example, the element may be pushed out by a blade.

What is claimed is:

1. In a chemical analysis element cartridge comprising a box-shaped cartridge body in which a plurality of chemical analysis elements are stacked and from which the chemical analysis elements are taken out one by one through a take-out port formed in one end of the cartridge body, the take-out port having a first opening portion which is opened through a first side wall of the cartridge body and through which one chemical analysis element can be passed and a second opening portion which opened through one end face of the cartridge body, wherein the improvement comprises that a first engagement portion is formed on an outer surface of the first side wall adjacent the first opening portion and a second engagement portion is formed on the outer surface of a second side wall opposed to the first side wall;

a capping member having third and fourth engagement portions is removably mounted on the cartridge body to cover the first and second opening portions of the take-out port with the third and fourth engagement portions respectively engaged with the first and second engagement portions; and the capping member is provided with a protruding portion which projects into the cartridge body and pushes inside the chemical analysis element nearest to said one end face away from a take-out position where the protruding portion is aligned with the first opening portion.

2. A chemical analysis element cartridge as defined in claim 1 in which said capping member is substantially U-shaped and has first and second portions connected to opposite ends of the protruding portion, the first portion lying on the first side wall adjacent the first opening portion and the second portion lying on the second side wall when the capping member is on the cartridge body with the third and fourth engagement portions respectively engaged with the first and second engagement portions, said first and second engagement portions are in the form of recesses respectively formed on the outer surfaces of the first and second side walls, and said third and fourth engagement portions are in the form of projections respectively formed on inner surfaces of the first and second portions of the capping member adjacent or on the ends of the first and second portions.

3. A chemical analysis element cartridge as defined in claim 2 in which said first portion of the capping member is longer than the second portion and a free end portion of the second portion extends obliquely outward so that an end of the second portion is positioned away from the second side wall.

4. A chemical analysis element cartridge as defined in claim 2 in which said second portion has an inclined engagement surface facing toward the protruding portion.

5. A chemical analysis element cartridge as defined in claim 2 in which said first portion is inserted between a pair of ribs formed on the first side wall to extend in a longitudinal direction of the cartridge body.

6. In a chemical analysis element cartridge comprising a box-shaped cartridge body in which a plurality of chemical analysis elements are stacked and from which the chemical analysis elements are taken out one by one through a take-out port formed in one end of the cartridge body, the take-out port having a first opening portion which is opened through a first side wall of the cartridge body and through which one chemical analysis element can be passed and a second opening portion which opened through one end face of the cartridge body, wherein the improvement comprises that a first engagement portion is formed on an outer surface of the first side wall adjacent the first opening portion and a second engagement portion is formed on the outer surface of a second side wall opposed to the first side wall;

a capping member having third and fourth engagement portions is removably mounted on the cartridge body to cover the first and second opening portions of the take-out port with the third and fourth engagement portions respectively engaged with the first and second engagement portions; and the capping member is provided with a protruding portion which projects into the cartridge body and pushes inside the chemical analysis element nearest to said one end face away from a take-out position wherein the protruding portion is aligned with the first opening portion, and wherein the protrusion portion has a first portion connected to an end thereof and said first portion is inserted between a pair of ribs formed in the first side wall and extend in a longitudinal direction of the cartridge body.

* * * * *